United States Patent
Rosenzweig

(10) Patent No.: US 11,154,277 B2
(45) Date of Patent: Oct. 26, 2021

(54) TISSUE VISCOELASTIC ESTIMATION FROM SHEAR VELOCITY IN ULTRASOUND MEDICAL IMAGING

(71) Applicant: Siemens Medical Solutions USA, Inc., Malvern, PA (US)

(72) Inventor: Stephen J. Rosenzweig, Seattle, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 538 days.

(21) Appl. No.: 15/798,932

(22) Filed: Oct. 31, 2017

(65) Prior Publication Data

US 2019/0125308 A1    May 2, 2019

(51) Int. Cl.
*A61B 8/08* (2006.01)
*A61B 8/00* (2006.01)

(52) U.S. Cl.
CPC ............ *A61B 8/485* (2013.01); *A61B 8/5207* (2013.01); *A61B 8/4494* (2013.01); *A61B 8/461* (2013.01); *A61B 8/5223* (2013.01)

(58) Field of Classification Search
CPC ......... A61B 8/08; A61B 8/5207; A61B 8/461; A61B 8/4494; A61B 8/5223; A61B 8/485; A61B 8/587; A61B 8/4444; A61B 34/25; A61B 2090/378; A61N 7/00; A61N 7/02; G16H 50/30; G01S 15/8993; G01S 15/899; G01S 7/52036; G01S 7/52042
USPC .................................................. 600/438, 407
See application file for complete search history.

(56) References Cited

U.S. PATENT DOCUMENTS

| | | | | |
|---|---|---|---|---|
| 8,225,666 | B2* | 7/2012 | McAleavey | A61B 8/485 73/602 |
| 8,394,026 | B2* | 3/2013 | Eskandari | A61B 8/587 600/438 |
| 10,376,233 | B2 | 8/2019 | Labyed et al. | |
| 10,582,911 | B2 | 3/2020 | Labyed et al. | |
| 2004/0167403 | A1* | 8/2004 | Nightingale | A61B 5/0053 600/437 |
| 2004/0260180 | A1* | 12/2004 | Kanai | A61B 8/0858 600/449 |
| 2005/0119568 | A1* | 6/2005 | Salcudean | A61B 8/485 600/437 |
| 2005/0267695 | A1* | 12/2005 | German | G01N 3/30 702/41 |

(Continued)

FOREIGN PATENT DOCUMENTS

| | | |
|---|---|---|
| CN | 106419961 | 2/2017 |
| CN | 107260210 | 10/2017 |

(Continued)

OTHER PUBLICATIONS

Translation of JP2017104526A (Year: 2017).*

(Continued)

*Primary Examiner* — Oommen Jacob

(57) ABSTRACT

For viscoelastic estimation with ultrasound, shear wave speed is measured for different locations in a region of interest. For each location, the shear wave speed is estimated without frequency band division. A distribution of shear wave speeds in the region of interest is matched a modeled distribution corresponding to a particular value of the viscoelastic property.

12 Claims, 3 Drawing Sheets

(56) References Cited

U.S. PATENT DOCUMENTS

| | | | |
|---|---|---|---|
| 2007/0038095 A1* | 2/2007 | Greenleaf | A61B 8/485 600/438 |
| 2008/0249408 A1* | 10/2008 | Palmeri | A61B 8/485 600/438 |
| 2009/0149750 A1* | 6/2009 | Matsumura | A61B 5/0048 600/438 |
| 2009/0216119 A1* | 8/2009 | Fan | A61B 5/0048 600/438 |
| 2010/0016718 A1* | 1/2010 | Fan | G01S 7/52042 600/438 |
| 2010/0130861 A1* | 5/2010 | Shimazaki | A61B 8/5238 600/443 |
| 2010/0138163 A1* | 6/2010 | Gallippi | G01N 29/045 702/19 |
| 2010/0170342 A1 | 7/2010 | Sinkus et al. | |
| 2010/0179413 A1* | 7/2010 | Kadour | A61B 8/5238 600/411 |
| 2010/0317971 A1* | 12/2010 | Fan | G01S 15/8993 600/439 |
| 2011/0063950 A1* | 3/2011 | Greenleaf | A61B 8/485 367/87 |
| 2011/0319756 A1* | 12/2011 | Zheng | G01S 7/52036 600/438 |
| 2012/0136250 A1* | 5/2012 | Tabaru | G01S 7/52026 600/438 |
| 2012/0215101 A1* | 8/2012 | Maleke | A61B 8/08 600/438 |
| 2012/0226158 A1* | 9/2012 | Greenleaf | A61B 6/5217 600/438 |
| 2013/0211253 A1* | 8/2013 | Hsu | G01S 15/8915 600/438 |
| 2014/0018679 A1* | 1/2014 | Chen | G01S 7/52042 600/438 |
| 2014/0046173 A1* | 2/2014 | Greenleaf | G01N 29/075 600/411 |
| 2014/0081138 A1 | 3/2014 | Bercoff et al. | |
| 2014/0187904 A1* | 7/2014 | Razani | A61B 5/0048 600/407 |
| 2014/0221833 A1* | 8/2014 | Oikawa | A61B 8/4483 600/438 |
| 2014/0316267 A1* | 10/2014 | Barry | A61B 8/085 600/438 |
| 2015/0005632 A1* | 1/2015 | Sakaguchi | G01S 7/52042 600/438 |
| 2015/0005633 A1* | 1/2015 | Kanayama | G01S 15/8915 600/438 |
| 2015/0216507 A1 | 8/2015 | Song et al. | |
| 2015/0305719 A1* | 10/2015 | Nenadic | A61B 8/5223 600/438 |
| 2016/0274067 A1* | 9/2016 | Walker | G01N 29/036 |
| 2016/0302769 A1 | 10/2016 | Labyed et al. | |
| 2016/0310107 A1* | 10/2016 | Mansi | A61B 8/485 |
| 2018/0098752 A1* | 4/2018 | Rouze | G16H 50/30 |

FOREIGN PATENT DOCUMENTS

| | | |
|---|---|---|
| EP | 2881041 A1 | 10/2015 |
| JP | 2017104526 A | 6/2017 |
| KR | 20150130093 A | 11/2015 |
| KR | 20170085516 A | 7/2017 |
| WO | 2016209922 A1 | 12/2016 |
| WO | 2017107660 A1 | 6/2017 |

OTHER PUBLICATIONS

Chen ["Complex Stiffness Quantification Using Ultrasound Stimulated Vibrometry", 2003 IEEE Ultrasonics Symposium-941], (Year: 2003).*

Chen ["Assessment of Liver Viscoelasticity by Using Shear Waves Induced by Ultrasound Radiation Force", Radiology: vol. 266 : No. 3—Mar. 2013] (Year: 2013).*

Sloun ["Viscoelasticity Mapping by Identification of Local Shear Wave Dynamics", IEEE Transactions on Ultrasonics, Ferroelectrics, and Frequency Control, vol. 64, No. 11, Nov. 2017 ] (Year: 2017).*

Yeh ["Shear-Wave Elasticity Imaging of a Liver Fibrosis Mouse Model Using High-Frequency Ultrasound", IEEE Transactions on Ultrasonics, Ferroelectrics, and Frequency Control, vol. 62, No. 6, Jun. 2015] (Year: 2015).*

Mauldin, F.W., et al., "Monitored steady-state excitation and recovery (MSSR) radiation force imaging using viscoelastic models," IEEE Transacations on Ultrasonics, Ferroelectronics, and Frequency Control, IEEE, US, vol. 55, No. 7, Jul. 2008.

Search Report Received for Corresponding French Application No. 1871208, dated Oct. 29, 2019.

Chen, Shigao, Mostafa Fatemi, and James F. Greenleaf. "Quantifying elasticity and viscosity from measurement of shear wave speed dispersion." The Journal of the Acoustical Society of America 115.6 (2004): 2781-2785.

Deffieux, Thomas, et al. "Shear wave spectroscopy for in vivo quantification of human soft tissues visco-elasticity." IEEE transactions on medical imaging 28.3 (2009): 313-322.

Nightingale, Kathryn R., et al. "Derivation and analysis of viscoelastic properties in human liver: impact of frequency on fibrosis and steatosis staging." IEEE transactions on ultrasonics, ferroelectrics, and frequency control 62.1 (2015).

Rouze, Ned C., Mark L. Palmeri, and Kathryn R. Nightingale. "Estimation of model parameters characterizing dispersion in ARFI induced shear waves in in vivo human liver." Ultrasonics Symposium (IUS), 2014 IEEE International. IEEE, 2014.

* cited by examiner

TISSUE VISCOELASTIC ESTIMATION FROM SHEAR VELOCITY IN ULTRASOUND MEDICAL IMAGING

BACKGROUND

The present embodiments relate to tissue characterization using ultrasound imaging.

Tissue of a patient may be characterized by measuring tissue response to stress. Tissue displacement is caused by a wave generated from a stress, such as an acoustic force radiation impulse (ARFI). The tissue response to the wave is tracked over time, providing an indication of elasticity. A variety of tissues, including liver, are more appropriately modeled as viscoelastic media rather than elastic media. The primary characteristic of shear wave propagation in viscoelastic media is that the media has a complex wave number corresponding to a frequency-dependent shear wave speed and shear wave attenuation.

The current state of the art for estimating viscoelastic properties of tissue using ARFI-based shear wave imaging is performed by estimating phase velocities in the Fourier domain. To estimate the phase velocities, the tissue displacement signal is divided into small frequency bands, and the shear wave speed is then independently estimated in each of the frequency bands. The amount of signal in each of these bands is low, and therefore the estimates are prone to noise and have not been demonstrated to be practical in vivo.

SUMMARY

By way of introduction, the preferred embodiments described below include methods, instructions and systems for viscoelastic estimation with ultrasound. Shear wave speed is measured for different locations in a region of interest. For each location, the shear wave speed is estimated without frequency band division. A distribution of shear wave speeds in the region of interest is matched to a modeled distribution corresponding to a particular value of the viscoelastic property.

In a first aspect, a method is provided for viscoelastic estimation by an ultrasound imaging system. A pushing pulse is transmitted from a transducer. The pushing pulse generates a shear wave in tissue of a patient. The ultrasound imaging system tracks tissue displacements at a plurality of locations in a region of interest. The tissue displacements are in response to the shear wave. Shear wave speeds of the shear wave in the tissue of the patient are determined as a function of lateral distances from an origin of the shear wave in the tissue of the patient from the tissue displacements. A viscoelastic parameter is estimated as a function of a distribution of the shear wave speeds. An image showing of the estimate of the viscoelastic parameter is generated.

In a second aspect, a method is provided for viscoelastic estimation by an ultrasound imaging system. The ultrasound imaging system measures shear wave velocities at different locations in tissue of a patient. The shear wave velocities of the different locations are matched with a reference. The reference is labeled with a value of a viscoelastic property. The value of the viscoelastic property assigned to the tissue of the patient is transmitted.

In a third aspect, a system is provided for viscoelastic estimation with ultrasound. An ultrasound scanner is configured to transmit an acoustic radiation force pulse from a transducer into tissue and to scan the tissue as it responds to the acoustic radiation force pulse. An image processor is configured to measure velocities for the tissue response for a plurality of locations from the scan and determine a value of a viscoelastic property of the tissue based on a spatial variance of the velocities. A display is configured to display an image showing the value of the viscoelastic property of the tissue.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Tissue viscoelastic properties may be quantified utilizing travel-distance-based shear wave speeds. Rather than estimating phase velocities, the quantification relies on group velocity (i.e., shear wave speed without Fourier analysis or separation by frequency). Traditional shear wave speed imaging provides group velocity measures where information at various frequencies are mixed together, providing a higher signal level. Rather than interpreting the shear wave speed as a function of frequency, the group velocity is used.

To provide information about the viscoelastic properties of the tissue, the shear wave tracking region is divided into multiple sub regions defined by the starting distance from the shear wave source and the total propagation distance. The shear wave speed is then estimated for each of these sub regions. The resulting set of speeds is correlated back to viscoelastic models to determine one or more viscoelastic properties of the tissue.

Due to the increase in signal-to-noise ratio as compared to determining speed as a function of frequency, the sensitivity and/or specificity of estimation of the viscoelastic property is improved. This may allow implementation in ultrasound scanners used with patients, assisting physicians in non-invasive evaluation of fibrosis detection, steatosis quantification, differentiation of benign and malignant breast cancers, and/or compensation for increased shear wave speed estimates caused by tissue compression.

Figure 1:
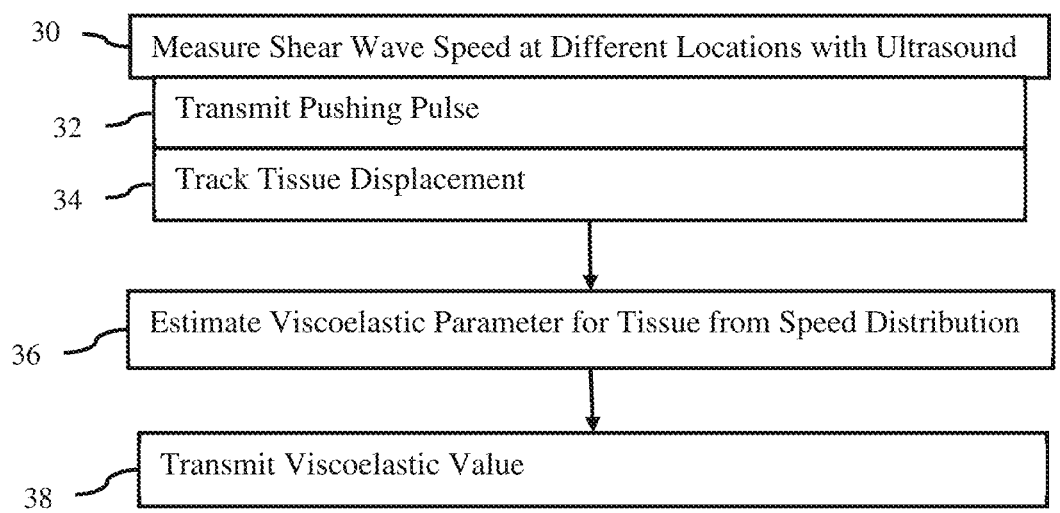
FIG. 1 is a flow chart diagram of one embodiment of a method for viscoelastic estimation by an ultrasound imaging system.

FIG. 1 shows a method for viscoelastic estimation by an ultrasound imaging system. Due to attenuation of a shear wave in viscoelastic tissue, velocities of different distances from the origin of the shear wave have different values. In general, a spatial distribution of estimates of shear wave speeds in a region of interest of a patient is matched to a modeled distribution with a known value of the viscoelastic characteristic. That known value is the value used for the patient.

Figure 5:
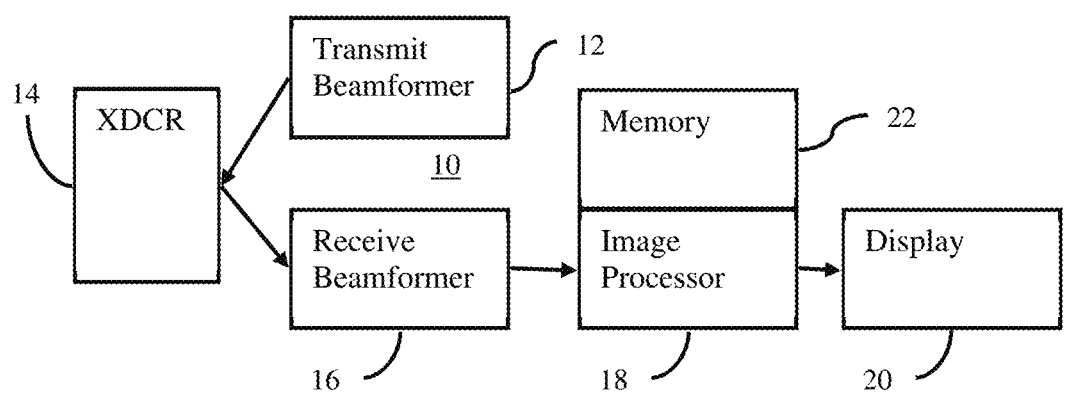
FIG. 5 is a block diagram of one embodiment of a system for viscoelastic estimation with ultrasound.

The acts are performed with an ultrasound imaging system, such as the system described for FIG. 5. A transducer and/or beamformers are used to acquire data, and a image processor estimates displacements from the data and shear wave speeds from the displacements. The image processor estimates the viscoelastic parameter. The ultrasound imaging system outputs the value of the viscoelastic parameter. Other devices, such as a computer or detector, may be used to perform any of the acts.

Additional, different or fewer acts may be provided in the method of FIG. 1. For example, act 38 is not provided. As another example, other acts than acts 32 and 34 are used to measure the shear wave speed.

The acts are performed in the order described or shown (e.g., top to bottom or numerical). Other orders may be provided, such as by repeating the acts for another region of interest or repeating act 30 to expand the region for which the viscoelastic parameter is estimated in act 36.

In act 30, the ultrasound system measures shear wave velocities at different locations in tissue of a patient. The velocities are measured based on a travel distance and timing of a shear wave propagating from an origin to different locations in a region of interest. Shear wave velocity imaging is performed with separate values of shear wave velocity being measured for different locations.

The shear wave velocities are based on tissue displacements. The ultrasound system acquires tissue displacements over time (i.e., displacement profiles), but tissue displacement as a function of location for each of different times may be used. An ARFI (e.g., pushing pulse or acoustic radiation impulse excitation) or other source of stress generates a shear wave in tissue. As the shear wave propagates through the tissue, the tissue displaces. By scanning the tissue with ultrasound, the data for calculating the displacements over time is acquired. Using correlation or other similarity measure, the displacements represented by the scans acquired at different times are determined.

Acts 32 and 34 provide one example of acquiring tissue displacements. Additional, different, or fewer acts may be provided for acquiring tissue displacements.

In act 32, a beamformer generates electrical signals for focused ultrasound transmission and a transducer converts the electrical signals to acoustic signals for transmitting the pushing pulse from the transducer. ARFI is used. An acoustic excitation is transmitted into a patient. The acoustic excitation acts as an impulse excitation for causing displacement. For example, a 400 cycle transmit waveform with power or peak amplitude levels similar or lower than B-mode transmissions for imaging tissue is transmitted as an acoustic beam. In one embodiment, the transmission is a shear wave generating sequence applied to the field of view. Any ARFI or shear wave imaging sequence may be used. Other sources of stress may be used, such as a thumper (mechanical impact or vibration source).

The transmission is configured by power, amplitude, timing, or other characteristic to cause stress on tissue sufficient to displace the tissue at a focal location. For example, a transmit focus of the beam is set relative to a field of view or region of interest (ROI) to cause the generated shear wave displacement throughout the field of view or ROI.

The impulse excitation generates a shear wave at a spatial location. Where the excitation is sufficiently strong, the shear wave is generated. The shear wave propagates transversely through tissue more slowly than the longitudinal wave propagates along the acoustic wave emission direction, so the type of wave may be distinguished by timing and/or direction. The displacement of the tissue due to the shear wave is greater at locations closer to the focal location at which the wave is generated. As the wave travels, the magnitude of the wave attenuates.

In act 34, tissue displacements are tracked. The ultrasound system, such as an image processor of the system, tracks the displacements in response to the pushing pulse. For each of a plurality of locations, the displacement caused by the propagating shear wave is tracked. The tracking is axial (i.e., tracking displacements one-dimensionally along a scan line), but may be two or three-dimensional tracking.

The tracking is over time. The tissue displacements for each location are found for any number of temporal samplings over a period during which the wave is expected to propagate by the location. By tracking at multiple locations, tissue displacement profiles of displacement over time for the different locations are provided.

The period for tracking may include times prior to the transmission of the pushing pulse and/or shear wave reaching each given location. Similarly, the period for tracking may include times after the tissue relaxes or the entire shear wave has propagated past each location. While the shear wave propagates past the locations, the tissue is scanned.

A transducer and beamformer acquire echo data at different times to determine the displacement of the tissue. The displacement is detected with ultrasound scanning. Ultrasound data is obtained. At least some of the ultrasound data is responsive to displacement caused by the shear wave or pressure. A region, such as a region of interest, entire field of view, or sub-region of interest, is scanned with ultrasound. The region is monitored to detect the wave. The echo data represents the tissue when subjected to different amounts of pressure at different times. The region is any size, such as 5×5 mm in lateral and 10 mm in axial. For example, B-mode scans are performed to detect tissue displacement. Any sampling or beamformer resolution may be used, such as measuring on a linear grid with sample locations every 0.25 mm. Doppler, color flow, or other ultrasound mode may be used to detect displacement.

For a given time, ultrasound is transmitted to the tissue or region of interest. Any now known or later developed displacement imaging may be used. For example, pulses with 1-5 cycle durations are used with an intensity of less than 720 mW/cm$^2$. Pulses with other intensities may be used. The scanning is performed for any number of scan lines. For example, eight or sixteen receive beams distributed in two-dimensions are formed in response to each transmission. After or while applying stress, B-mode transmissions are performed repetitively along a single transmit scan line and receptions along adjacent receive scan lines. In other embodiments, only a single receive beam or other numbers of receive beams are formed in response to each transmission. Additional transmit scan lines and corresponding receive line or lines may be used. Any number of repetitions may be used, such as about 120 times or over 15 ms.

The B-mode intensity may vary due to displacement of the tissue over time. For the monitored scan lines, a sequence of data is provided representing a time profile of tissue motion resulting from the stress. By performing the transmitting and receiving multiple times, data representing the region at different times is received. By repetitively scanning with ultrasound, the position of tissue at different times is determined.

The displacement is detected for each of multiple spatial locations. For example, the velocity, variance, shift in intensity pattern (e.g., speckle tracking), or other information is detected from the received data as the displacement between two times. An ongoing or sequence of displacements may be detected for each of the locations.

In one embodiment using B-mode data, the data from different scans is axially correlated as a function of time. For each depth or spatial sampling position, a correlation over a plurality of depths or spatial sampling positions (e.g., kernel of 64 depths with the center depth being the point for which the profile is calculated) is performed. For example, a current set of data is correlated multiple times with a reference set of data. The location of a sub-set of data centered at a given location in the reference set is identified in the current set. Different relative translations between the two data sets are performed.

The reference is a first or other set of data or data from another scan. The reference set is from before the stress, but may be from after the stress. The same reference is used for the entire displacement detection, or the reference data changes in an ongoing or moving window.

The level of similarity or correlation of the data at each of different offset positions is calculated. The translation with a greatest correlation represents the displacement or offset for the time associated with the current data being compared to the reference.

Any now known or later developed correlation may be used, such as cross-correlation, pattern matching, or minimum sum of absolute differences. Tissue structure and/or speckle are correlated. Using Doppler detection, a clutter filter passes information associated with moving tissue. The velocity of the tissue is derived from multiple echoes. The velocity is used to determine the displacement towards or away from the transducer. Alternatively, the relative or difference between velocities at different locations may indicate strain or displacement.

Figure 2:
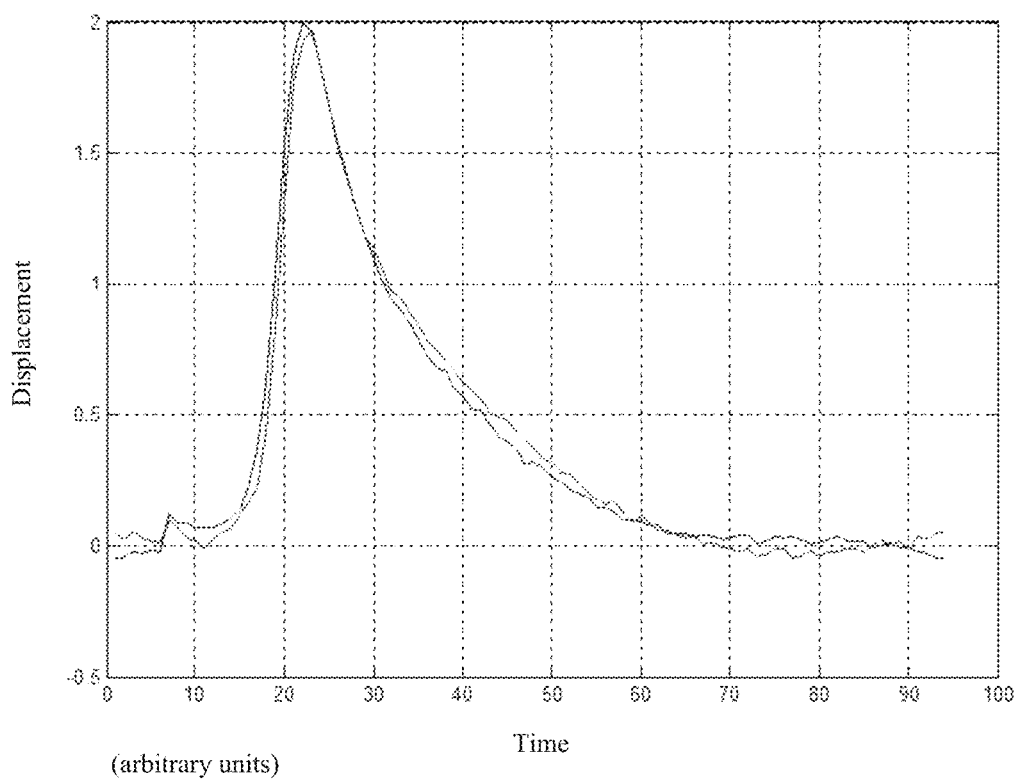
FIG. 2 shows two example displacement profiles.

FIG. 2 shows two example displacement profiles of displacements over time for two adjacent locations. The displacement of the tissue starts from a steady state from prior to the shear wave arriving, then the displacement increases to a maximum, and after which the displacement decays back to the steady state. Other displacement profiles are possible. Any number of sample positions may be measured for displacement, such as measuring every quarter millimeter in the 10×5 mm region of interest. The displacement profile is determined at each sample point or data from two or more sample points are combined to give a displacement profile for a sub region. Displacement for each sample point and for each sample time is measured.

The displacements over time and/or space are used for calculation. In one embodiment, the displacements for different depths are combined, leaving displacements spaced in azimuth and/or elevation. For example, the displacements for a given scan line or lateral location are averaged over depth. As an alternative to averaging, a maximum or other selection criterion is used to determine the displacement for a given lateral location. Displacements for only one depth may be used. Displacements for different depths may be used independently.

The tracking region is divided into multiple sub regions (e.g., 1 mm×1 mm). Each of the sub region is defined by the starting distance from the shear wave source (i.e., focal position) and the total propagation distance from the focal position to the sub region. Each sub region includes only one or more sample positions.

The entire receive signal is used for tracking. Rather than separating receive signals for separate tracking by frequency and/or estimating the shear wave speed from displacement profiles separated by frequency, the tracking uses the group shear wave speed. The receive signals and/or displacements are not separated by frequency, providing more robust estimation of shear wave speed.

Returning to act 30, the image processor determines the shear wave speeds of the shear wave in the tissue. A separate shear wave speed is estimated for each location, such as each sub-region or as a function of lateral distance from an origin of the shear wave. Where the sub-region includes multiple sample points, the arrival time of the shear wave is determined at each sample point individually. A linear regression between arrival time and lateral position is performed, and the slope of the linear regression is estimated as the shear wave speed. The arrival time is determined from the displacements. The shear wave speed is computed across multiple sample points in the sub-region. Other combination functions may be used, such as calculating shear wave speed for each sample point and then combining the shear waves speeds of the same sub-region (e.g., average, median, maximum, or minimum selection). The resulting shear wave speed as a function of location or sub-region provides a distribution of shear wave speed in the tissue. This distribution varies due to the viscoelastic characteristic of the tissue.

The displacements for a given sample point may be used for more than one estimate of shear wave speed. For example, the same ROI is divided into different sub regions, such as 1 mm×1 mm sub regions and 2 mm by 2 mm sub regions. Different starting and ending sample points define a given sub region. The shear velocity is determined in each of the sub regions individually. Alternatively, the velocity between the start and end locations of the sub region is calculated, such as finding a phase shift in the displacement profiles relative to the distance from the start to the end of the sub region.

The shear wave speed is based on the displacements as a function of time and/or location. The value of the shear wave speed for each sub region or location is estimated from the displacement profile or profiles. To estimate the value in one embodiment, the peak or maximum amplitude in the displacement profile is determined. Based on a distance of the location (i.e., sub region center, end point or start point) from the source of the stress (e.g., ARFI focal position or shear wave origin), a difference in time between application of the stress and the peak amplitude indicates a velocity. In an alternative approach, the displacement profiles from different locations are correlated to find a delay or phase difference between the locations. This phase shift may be used to calculate the velocity between the locations associated with the correlated profiles. In other embodiments, analytic data is calculated from the displacement profile and phase shift is used to determine the elasticity. A difference in phase over time of the displacements of different sub regions or a zero crossing of the phase for a given sub region indicates a velocity. In yet another embodiment, the displacement as a function of location for a given time indicates a location of maximum displacement. The distance from the shear wave origin to that location and the time provide the velocity. This is repeated for other times to find the maximum velocity at each location.

Figure 3:
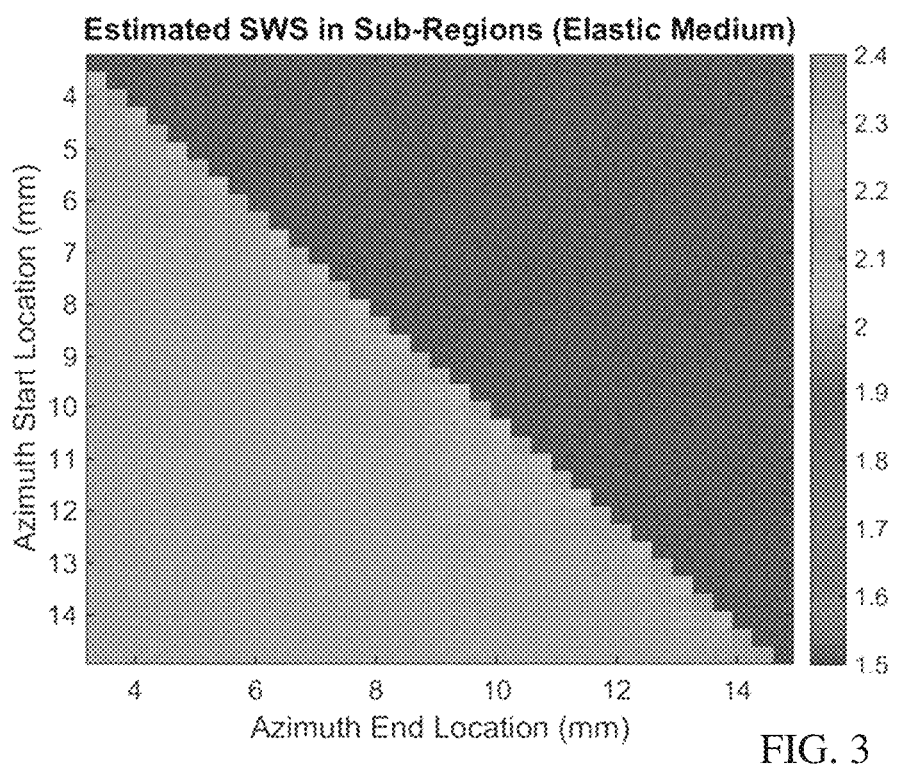
FIG. 3 shows an example spatial distribution of shear wave speed in an elastic medium.
Figure 4:
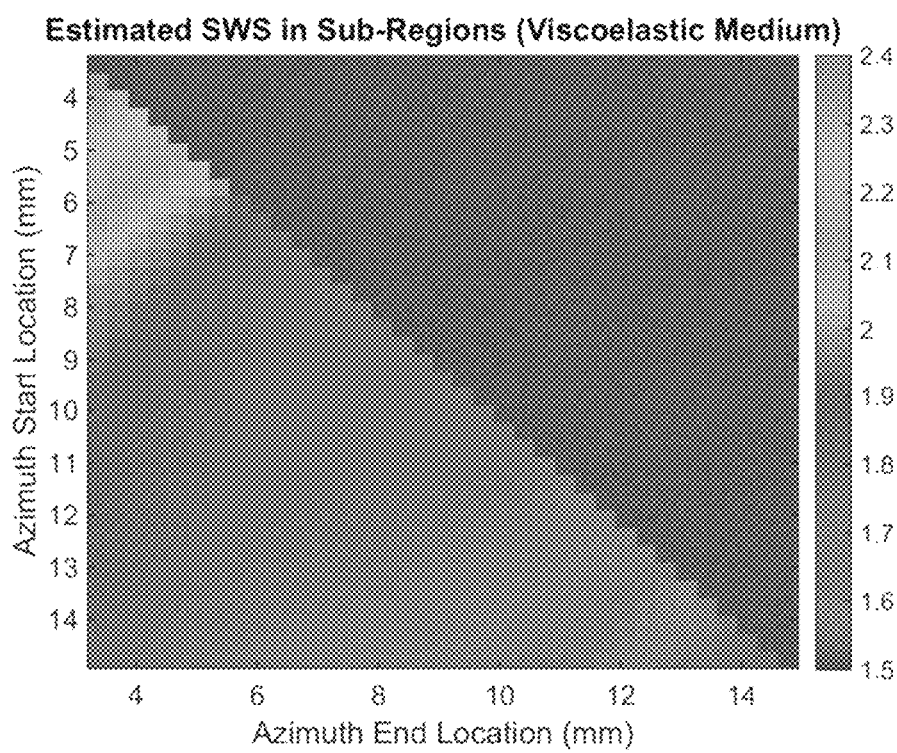
FIG. 4 shows an example spatial distribution of shear wave speed in a viscoelastic medium.

A shear wave speed is provided for each sub region. With different sized sub regions, different shear wave speeds are provided. For example, sub regions of one size are used to determine shear wave velocities for the sub regions, and sub regions of another size use the same data to determine other shear wave velocities for those sub regions. Any number of sizes of sub regions may be used. FIGS. 3 and 4 show two examples of simulated shear velocities from the same data determined with various azimuth start and end locations for each sub region. Different sub regions are provided for different determination of the shear velocity from travel distance from the ARFI focal position or between edges of the sub regions. Alternatively, the shear wave speeds for one set of sub regions provide the distribution (i.e., a field of velocities in a 2D or 3D region for each location with a same sample size (e.g., 1 mm×1 mm)).

In act 36 of FIG. 1, the image processor estimates a viscoelastic parameter. Any viscoelastic parameter may be estimated, such as the viscosity, Young's modulus, or complex modulus. Any parameterization of viscoelastic behavior of tissue may be used. Other characteristics of the tissue, such as the elasticity, may be estimated in the same way. The other characteristics are estimated independently of or simultaneously with the viscoelastic parameter.

The estimate is for the region of interest. The distribution of shear wave speeds by location of the sub regions is used to estimate a value of the viscoelastic parameter for the region or ROI. The variance of the velocities or shear wave speeds in the distribution indicates the value of the viscoelastic characteristic of the tissue. If the tissue is purely elastic, then all the speeds estimated in the sub regions are identical. FIG. 3 shows the shear wave speeds as being similar, indicating a mostly elastic tissue. As the viscosity of the tissue increases, the sub regions will have more widely varying shear wave speed estimates. FIG. 4 shows variance in the shear wave speeds, indicating the tissue as viscoelastic. In viscoelastic media, due to transverse (e.g., shear) wave attenuation, the estimated shear wave speed depends on the starting azimuth location for estimation as well as the propagation distance from the shear wave origin or across the sub region. By estimating the transverse shear wave speed with multiple start and end azimuth locations, information about the viscoelastic properties of the media may be derived.

The value of the viscoelastic parameter is estimated using the distribution. The variance in the distribution may be measured as a statistical value, such as a standard deviation or other indication of variability. This calculation may be related to the value of the viscoelastic parameter by look up table, empirically determined function, or by a machine-learnt classifier.

In another embodiment, the distribution is matched with a reference. A viscoelastic model is used to create distributions for the tissue of interest (e.g., liver). Any viscoelastic model may be used, such as Voigt or Maxwell models of elasticity and viscosity. Other models include a standard linear solid model with the viscoelastic parameter between the 0 frequency and infinite frequency stiffness parameters. The model simulates the shear wave speeds given different values of the viscoelastic parameter. The values of the other parameters of the model are constant or also vary, such as being based on the tissue of interest. The simulation provides reference distributions or fields of shear wave speeds for corresponding or respective values of the viscoelastic parameter. Alternatively, the reference distributions are created empirically, such as with measurements performed with phantoms having different known values of the viscoelastic parameter or comparisons of measured shear wave velocities with tissue having known values of the viscoelastic parameter (e.g., a database based on resected or biopsied tissue). By imaging viscoelastic phantoms that correspond to different viscoelastic values, references for different values of the viscoelastic property are created. Other references and corresponding values of viscoelastic parameters may be created by interpolation.

The references labeled with different values of the viscoelastic parameter are used to match with the spatial distribution of velocities measured for the patient. Any matching may be used, such as a correlation. A level of correlation between the measured distribution for the patient and each or some of the references may be used. Any search pattern or criterion may be used, such as selecting a next reference to check based on a direction and/or amount of difference between a previous correlation or between a set of previous correlations. Any measure of correlation may be used, such as cross-correlation or minimum sum of absolute differences.

The set of speeds is correlated back to the viscoelastic models, whether empirical or computationally simulated, to determine the viscoelastic property or properties of the tissue. If the tissue is purely elastic, then all the speeds estimated in the sub regions are identical. As the viscosity of the tissue increases, the sub regions will have more widely varying shear wave speed estimates. The reference with a greatest match (e.g., highest correlation) to the distribution of velocities for the patient is selected. The label of the value or values of the viscoelastic parameter and any other parameters (e.g., elasticity) from the matching reference are assigned to the patient. The labeled value from the reference is the estimated value of the viscoelastic parameter for the patient.

In act 38, the image processor transmits the value of the viscoelastic property assigned to the tissue of the patient. The transmission is to a display, memory, or network. For example, the transmission is an output from or within the ultrasound imaging system.

In one embodiment, an image is output. The value for the ROI is provided on a shear wave velocity image, B-mode image, or other ultrasound image. For example, a shear wave velocity image has color modulated based on shear velocity as a function of location in the ROI. The shear wave velocity image is overlaid on a B-mode image covering a larger field of view than the ROI or shear wave velocity image. The value of the viscoelastic parameter is provided as a text annotation over or adjacent to the shear wave velocity and/or B-mode image. Alternatively, the brightness, tent, hue, or color map is based on the value of the viscoelastic parameter. In other embodiments, other types of elasticity imaging, no shear or elasticity image, and/or different types of ultrasound imaging are provided.

In another embodiment, the value for the viscoelastic parameter is output as text, a number, or coded in a graph. For example, the user selects a location on a B-mode image. In response, the ultrasound system calculates the value for the viscoelastic parameter of interest for an ROI about that selected location. A numerical, textual, and/or graphical representation of the calculated value is overlaid on the B-mode image, displayed independently, or otherwise communicated to the user (e.g., added to a report).

FIG. 5 shows one embodiment of a system 10 for viscoelastic estimation with ultrasound. The system 10 implements the method of FIG. 1 or other methods. The system 10 includes a transmit beamformer 12, a transducer 14, a receive beamformer 16, an image processor 18, a display 20, and a memory 22. Additional, different or fewer components may be provided. For example, a user input is provided for user interaction with the system, such as to select a location for which a measurement is to occur or to designate placement of an ROI.

The system 10 is a medical diagnostic ultrasound imaging system or ultrasound scanner. The system 10 is configured to transmit an acoustic radiation force impulse from the transducer 14 into tissue and to scan the tissue at a plurality of locations as the tissue responds to a shear wave created by the acoustic radiation force impulse. The response to the shear wave is tracked by the ultrasound scanner. In alternative embodiments, the system 10 includes a front-end scanner and a back-end processor, such as a personal computer, workstation, PACS station, or other arrangement at a same location or distributed over a network for real-time or post acquisition imaging. The scanning components (e.g., transmit beamformer 12, transducer 14, and receive beamformer 16) are part of a different device than the memory 22, image processor 18, and/or display 20. The back-end may acquire data from a memory or from transfer over a network. The front-end provides the data to the memory or network.

The transmit beamformer 12 is an ultrasound transmitter, memory, pulser, analog circuit, digital circuit, or combinations thereof. The transmit beamformer 12 is operable to generate waveforms for a plurality of channels with different or relative amplitudes, delays, and/or phasing. Upon transmission of acoustic waves from the transducer 14 in response to the generated electrical waveforms, one or more beams are formed. A sequence of transmit beams are generated to scan a region. Sector, Vector®, linear, or other scan formats may be used. In alternative embodiments, the transmit beamformer 12 generates a plane wave or diverging wave for more rapid scanning. The same region is scanned multiple times. For shear imaging, a sequence of scans along the same lines is used.

The same transmit beamformer 12 may generate impulse excitations (ARFI or pushing pulse) and acoustic beams for tracking. Electrical waveforms for ARFI are generated, and then electrical waveforms for tracking are generated. In alternative embodiments, a different transmit beamformer is provided for generating the ARFI than for tracking. The transmit beamformer 12 causes the transducer 14 to generate acoustic energy. Using delay profiles across channels, the transmit beamformer 12 steers the pushing pulse to the desired focal position or positions and scans the ROI for tracking displacements.

The transducer 14 is an array for generating acoustic energy from electrical waveforms. For an array, relative delays focus the acoustic energy. A given transmit event corresponds to transmission of acoustic energy by different elements at a substantially same time given the delays. The transmit event may provide a pulse of ultrasound energy for displacing the tissue. The pulse is an impulse excitation or tracking pulse. Impulse excitation includes waveforms with many cycles (e.g., 500 cycles) but that occurs in a relatively short time to cause tissue displacement over a longer time due to shear wave propagation. A tracking pulse may be B-mode transmission, such as using 1-5 cycles. The tracking pulses are used to scan a region of a patient undergoing a change in stress.

The transducer 14 is a 1-, 1.25-, 1.5-, 1.75- or 2-dimensional array of piezoelectric or capacitive membrane elements. A wobbler array may be used. The transducer 14 includes a plurality of elements for transducing between acoustic and electrical energies. Receive signals are generated in response to ultrasound energy (echoes) impinging on the elements of the transducer 14. The elements connect with channels of the transmit and receive beamformers 12, 16.

The receive beamformer 16 includes a plurality of channels with amplifiers, delays, and/or phase rotators, and one or more summers. Each channel connects with one or more transducer elements. The receive beamformer 16 is configured by hardware or software to apply relative delays, phases, and/or apodization to form one or more receive beams in response to each imaging or tracking transmission. Receive operation may not occur for echoes from the impulse excitation used to displace tissue. The receive beamformer 16 outputs data representing spatial locations using the receive signals. Relative delays and/or phasing and summation of signals from different elements provide beamformation. In alternative embodiments, the receive beamformer 16 is a processor for generating samples using Fourier or other transforms.

In coordination with the transmit beamformer 12, the receive beamformer 16 generates data representing a ROI at different times. After the ARFI, the receive beamformer 16 generates beams representing locations along one or a plurality of lines at different times. By scanning the ROI with ultrasound, data (e.g., beamformed samples) is generated. By repeating the scanning, ultrasound data representing the region at different times after the impulse excitation is acquired.

The receive beamformer 16 outputs beam summed data representing different sample positions. Dynamic focusing may be provided. The data may be for different purposes. For example, different scans are performed for B-mode or tissue data rather than for shear ultrasound imaging. Alternatively, the B-mode data is also used to determine a viscoelastic parameter value. As another example, data for shear imaging is acquired with a series of shared scans, and B-mode or Doppler scanning is performed separately or using some of the same data. The ultrasound or echo data is from any stage of processing, such as beamformed data before detection or data after detection.

The memory 22 is a non-transitory computer readable storage media. For example, the memory 22 is a cache, buffer, RAM, removable media, hard drive or other non-transitory computer readable storage media. Computer readable storage media include various types of volatile and nonvolatile storage media.

The memory 22 is configured by the image processor 18, a controller, or a memory processor to store and provide data. The memory 22 stores any of the data used to estimate the value for the viscoelastic parameter. For example, the ultrasound data (beamformed data and/or detected data), displacements, displacement profile, velocities, and/or model information are stored. The memory 22 is configured to store a plurality of spatial distributions of shear wave speed for different values of the viscoelastic property. The distributions may be formed as part of a look-up table, matrix of a machine-learnt classifier, or separate fields to be used as references. Each distribution is labeled with the respective value of the viscoelastic parameter. The memory 22 stores the measured distribution of velocities for the patient and/or correlation values of the measured distribution with multiple of the reference distributions.

The image processor 18 operates pursuant to instructions stored in the memory 22 or another memory for estimating a viscoelastic characteristic of tissue of a patient. The instructions for implementing the processes, methods and/or techniques discussed herein are provided on the computer-readable storage media or memories. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing, and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

The image processor 18 includes a B-mode detector, Doppler detector, pulsed wave Doppler detector, correlation processor, and/or Fourier transform processor for detecting and processing information for display from beamformed ultrasound samples.

In one embodiment, the image processor 18 includes one or more detectors and a separate processor. The separate processor is a control processor, general processor, digital signal processor, application specific integrated circuit, field programmable gate array, network, server, group of processors, graphics processing unit, digital signal processor, analog circuit, digital circuit, combinations thereof, or other now known or later developed device for estimating a viscoelastic parameter. For example, the separate processor is configured by hardware, firmware, and/or software to perform any combination of one or more of the acts 30-38 shown in FIG. 1.

The image processor 18 is configured to measure velocities for the tissue response for a plurality of locations from the scan. For example, the beamformed data or detected data are axially correlated with a reference to determine an amount of displacement of the tissue for a given time. The velocities are derived from the displacements.

The locations are sample positions of the receive beamformer 16 or sub regions of a ROI. Any sub region may include one or more sample positions. Where more than one sample position is included, the displacements from the multiple positions are used to estimate the shear wave speed for the sub-region (e.g., estimate from linear regression of arrival time given by the displacements). Alternatively, the velocities determined for the different sample positions of a sub region are averaged. Other combinations functions may be used, such as a median, maximum, or minimum.

The image processor 18 is configured to measure the velocities for different sub regions. For example, different starting and ending positions of the sub regions are used, providing velocities for different overlapping sub region arrangements (see FIGS. 3 and 4). Alternatively, a single division of the ROI into sub regions in a regular or irregular pattern is used.

The velocities are measured as shear wave speed. The shear wave generated in response to the acoustic radiation force caused time varying displacement at different locations. The image processor 18 calculates the velocity for each sub region from the distance from the origin of the shear wave to the center or other location of the sub region and the time of detection of the shear wave at the sub region based on the displacements as compared to the time of shear wave creation. Velocity across the sub region (i.e., from a start to an end of the sub region) may be used in other embodiments. A distribution of velocities for the region of interest is created.

The image processor 18 is configured to determine a value of a viscoelastic property of the tissue based on a spatial variance of the velocities. A measure of the variance itself and/or correlation of the spatial variance of the velocities with models or references generated from an empirical, phantom, or simulation (mathematical) model is used. The spatial variance maps to a value of the viscoelastic property. For example, the models or references correspond to respective values of the viscoelastic property. The value from the best matching or an interpolated value from the values of the two best matching models or references of spatial variance provide the value of the viscoelastic property for the tissue of the patient.

The image processor 18 is configured to generate one or more images. The image includes a color modulated region and/or alphanumeric text representing or based on the value of the viscoelastic property, such as an annotation on an image of a 2D or 3D representation of the tissue. For example, a shear wave velocity image is generated. Other elastography images may be generated, such as a shear modulus, strain, or strain rate image. The image is presented as an overlay or region of interest within a B-mode image. The viscoelastic property annotation is on, over, or adjacent to the spatial representation of the tissue. Alternatively or additionally, the value of the viscoelastic property is displayed as text, numerically, and/or in a graph separate from any spatial representation of the tissue, such as in a report.

The display 20 is a CRT, LCD, projector, plasma, or other display for displaying a value, two-dimensional images, or three-dimensional representations. The two-dimensional images represent spatial distribution in an area, such as a plane. The three-dimensional representations are rendered from the data representing spatial distribution in a volume. The display 20 is configured by the image processor 18 or other device by input of the signals to be displayed as an image. The display 20 displays an image representing the calculated value for an ROI. The image shows the value of the viscoelastic property of the tissue.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. A method for viscoelastic estimation by an ultrasound imaging system, the method comprising:

transmitting, from a transducer, a pushing pulse, the pushing pulse generating a shear wave in tissue of a patient;

tracking, by the ultrasound imaging system, tissue displacements at a plurality of locations in a region of interest, the tissue displacements being in response to the shear wave;

determining a plurality of shear wave speeds as a function of lateral distances from an origin of the shear wave in the tissue of the patient, the determining being from the tissue displacements;

estimating a viscoelastic parameter with a spatial distribution of the shear wave speeds, wherein estimating the viscoelastic parameter comprises correlating the spatial distribution of the shear wave speeds with references of spatially distributed speeds, each of the references labeled with different values of the viscoelastic parameter, and using the value of the viscoelastic parameter of the reference with a greatest correlation with the spatial distribution as the estimate; and generating an image showing of the estimate of the viscoelastic parameter.

2. The method of claim 1 wherein transmitting the pushing pulse comprises transmitting an acoustic radiation force impulse.

3. The method of claim 1 wherein tracking comprises determining the tissue displacements axially along a scan line over time, resulting in tissue displacement profiles over time for each of the locations.

4. The method of claim 3 wherein determining the shear wave speed comprises determining as a function of a phase shift in the displacement profiles.

5. The method of claim 1 wherein transmitting comprises transmitting the pushing pulse to a focal position, wherein tracking comprises tracking with the locations spaced laterally from the focal location, and wherein determining the shear wave speed comprises determining a shear wave velocity based on a distance from the focal position to the location and a time from the transmitting to a peak of the displacements at the location.

6. The method of claim 1 wherein estimating the viscoelastic parameter comprises estimating a viscosity of the tissue at the region of interest.

7. The method of claim 1 wherein the references comprise fields of velocities formed using the different values of the viscoelastic parameter in a viscoelastic model.

8. The method of claim 7 wherein the viscoelastic model comprises a Voigt, Maxwell or Standard Linear Solid model.

9. The method of claim 1 wherein tracking comprises tracking from received signals without frequency separation.

10. The method of claim 1 wherein generating the image comprises generating a B-mode image of the tissue with an alphanumeric text annotation of the estimate.

11. The method of claim 1 wherein the references comprise fields of velocities formed empirically.

12. A method for viscoelastic estimation by an ultrasound imaging system, the method comprising:

transmitting, from a transducer, a pushing pulse, the pushing pulse generating a shear wave in tissue of a patient;

tracking, by the ultrasound imaging system, tissue displacements at a plurality of locations in a region of interest, the tissue displacements being in response to the shear wave;

determining a plurality of shear wave speeds as a function of lateral distances from an origin of the shear wave in the tissue of the patient, the determining being from the tissue displacements;

estimating a viscoelastic parameter with a distribution of the shear wave speeds, wherein estimating the viscoelastic parameter comprises correlating the distribution with references and the references comprise fields of velocities formed using different values of the viscoelastic parameter in a viscoelastic model, and using the value of the viscoelastic parameter of the reference with a greatest correlation with the distribution as the estimate; and generating an image showing of the estimate of the viscoelastic parameter.

* * * * *